(12) United States Patent
Summers et al.

(10) Patent No.: US 7,074,812 B2
(45) Date of Patent: Jul. 11, 2006

(54) DEVELOPMENT OF MUSCLE MASS IN A MAMMAL

(75) Inventors: David P. Summers, Montgomery, TX (US); James Davidson, Alexandria, VA (US)

(73) Assignee: Nutraleutical Development Corporation, Montgomery, TX (US)

( * ) Notice: Subject to any disclaimer, the term of this patent is extended or adjusted under 35 U.S.C. 154(b) by 135 days.

(21) Appl. No.: 10/633,325

(22) Filed: Aug. 2, 2003

(65) Prior Publication Data

US 2004/0167179 A1    Aug. 26, 2004

Related U.S. Application Data

(60) Provisional application No. 60/400,649, filed on Aug. 2, 2002, provisional application No. 60/475,131, filed on Jun. 2, 2003.

(51) Int. Cl.
*A61K 31/44*      (2006.01)

(52) U.S. Cl. ..................................... 514/343

(58) Field of Classification Search ............... None
See application file for complete search history.

(56) References Cited

U.S. PATENT DOCUMENTS

| | | | |
|---|---|---|---|
| 5,212,188 A * | 5/1993 | Caldwell et al. | 514/343 |
| 5,232,932 A * | 8/1993 | Caldwell et al. | 514/343 |
| 6,277,855 B1 * | 8/2001 | Yerxa | 514/256 |
| 6,720,340 B1 * | 4/2004 | Cooke et al. | 514/343 |
| 2002/0192240 A1 * | 12/2002 | Brooks et al. | 424/247.1 |
| 2003/0176457 A1 * | 9/2003 | Coe et al. | 514/302 |

OTHER PUBLICATIONS

M. Korbling, et al. Adult stem cells for tissue repair-a new therapeutic concept?; NEJM, Aug. 7, 2003, vol. 349, Iss. 6, pp. 570-587, downloaded on Jul. 15, 2005 from http://www.innovitaresearch.org/news/04011301.html.*
Caterson et al., Application of Mesenchymal Stem Cells in Regeneration of Musculoskeletal Tissues, Feb. 5, 2001, Medscape General Medicine, 3(1), 2001, downloaded Jul. 15, 2005 from http://www.medscape.com/viewarticle/408101_print.*
Murphy, "Kicking butts:forget for a momment all that stuff about cancer—that's tomorrow. Smoking can screw up your workout today!", Men's Fitness, Nov. 2002, downloaded Jul. 15, 2005 from http://www.findarticles.com/p/articles/mi_m1608/is_11_18/ai_93009064/print.*
Hawke, "Muscle Stem Cells and Exercise Training", Exerc. Sport Sci Rev. 2005; 33 (2): 63-68, downloaded Jul. 15, 2005 from http://www.medscape.com/viewarticle/503050_print.*

* cited by examiner

*Primary Examiner*—Raymond J. Henley, III

(57) ABSTRACT

In a method of developing muscle mass in a mammal, nicotine or nicotine acetylcholine receptor agonist (nAChR) is administered in combination with exercise to stimulate, recruit and mobilize muscle cells to a specific muscle mass.

9 Claims, 2 Drawing Sheets

DEVELOPMENT OF MUSCLE MASS IN A MAMMAL

CROSS-REFERENCE TO RELATED APPLICATION

This application claims the benefit of U.S. Provisional Application Ser. No. 60/400,649, filed Aug. 2, 2002, and U.S. Provisional Application Ser. No. 60/475,131, filed Jun. 2, 2003, which applications are incorporated herein by reference.

BACKGROUND OF THE DISCLOSURE

The present invention relates generally to the field of development of muscle mass and body fitness; more specifically to a method utilizing a nicotine and/or nicotine acetylcholine receptor agonist supplement in combination with exercise to stimulate, recruit and mobilize new muscle cells to augment, strengthen or replace muscle cells in a mammalian body.

Development of muscle mass and body fitness is a multi-billion dollar industry worldwide. Myriad nutriceutical supplements and pharmacological medicines are utilized by wide ranging populations seeking to restore, augment or repair body tissues for both aesthetic and medical purposes. For example, stroke victims with muscle dystrophy require extensive rehabilitation of muscle use during recovery in order to restore muscle mass. Fitness devotees, and athletes seek to increase stamina, strength and muscle force in order to enhance personal appearance or performance. The very large population of persons wishing to aesthetically add muscle to body mass, replace fat with muscle or to simply increase strength in order to reduce fatigue stamina and/or appearance is accepted as a legitimate concern for good physiological and psychological health. Recent reports relate to anti-aging benefits when muscle-to-fat ratios are balanced.

Most, if not all health regimens relating to the above rely upon the effects of strenuous exercise programs supplemented with various nutritional diets. All require a relentless conformity to rigorous regimes, are costly and time consuming, and few result in any long-term success. Indeed, one of the common temptations for persons seeking to add muscle mass is the use of steroids, which have considerable negative side effects, including liver and heart damage.

It would seem that a process that enables the body to add or subtract various tissues through the use of the endogenous regulation of cells would be a major benefit to society. Recent reports of endogenous stem cells used to stimulate and promote the regrowth of de novo blood vessels to ischemic or injured tissues, such as the human heart, have been reported. Cooke J, et al., disclosed in PCT WO 01/08683 A1 the recruitment and mobilization of the body's own stem cells for building new blood vessels (angiogenesis) in blood-starved hind limbs in animals, through the use of nicotine in low dose forms. The cells that provided the new blood vessels originate, at least partly, in the patient's own bone marrow. Experiments demonstrated that after the animals were iatrogenically genically injured, then treated with nicotine, the area became mobilized with progenitor stem cells of both hematopoietic and mesenchymal lineage, which in turn differentiated into endothelial cells and smooth muscle cells. The use of nicotine for this purpose was also confirmed in a publication in the *American Journal of Pathology*, Vol. 161, No. 1, July 2002, Nicotine Accelerates Angiogenesis and Wound Healing in Genetically Diabetic Mice (Jacobi, et al). Scientists have reported that bone marrow stem cells injected directly into patients' hearts differentiated into cardiomyocyte (heart muscle) which repopulated the diseased and/or depleted muscle of the heart.

SUMMARY OF THE INVENTION

The present invention features a method of developing muscle mass by combining exercise with a nicotine or nicotine acetylcholine receptor agonist (nAChR) supplement to stimulate, recruit and mobilize muscle cells to a specific muscle mass.

DETAILED DESCRIPTION OF A PREFERRED EMBODIMENT

Figure 1:
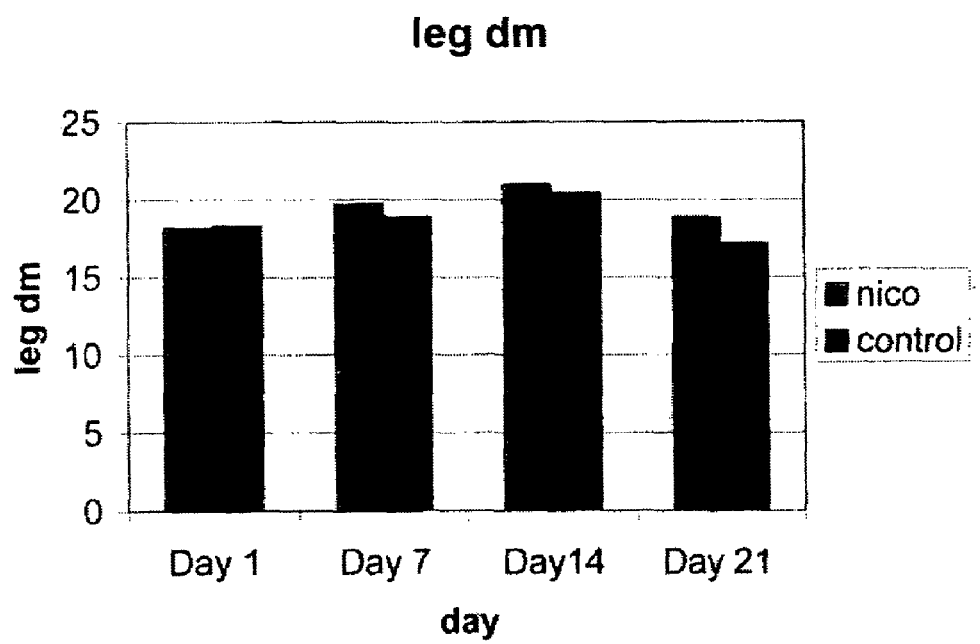
FIG. 1 is a graph illustrating the effect of a nicotine supplement on the leg diameter of an animal model.

The instant invention comprises a method of utilizing nicotine and/or nicotinic acetylcholine receptor agonist (nAChR) to stimulate, recruit and mobilize new muscle cells to augment, strengthen, or replace muscle cells in a mammalian body. This is accomplished by administering nicotine to a mammalian body in amounts sufficient to stimulate, recruit and mobilize muscle cells to a specific muscle mass. The muscle cells may be differentiated from stem cells which may be endogenous or exogenous. The muscle cells are recruited to a specific muscle mass of the body by training exercise. The training exercise results in the specific muscle mass exceeding the cell replenishing effects of a normal life style. The training exercise causes an abnormal physiologic response in the specific muscle mass, thereby causing release of various metabolites, catecholamines, cytokines, chemokines, and/or an inflammatory response to further enhance the increase of tissue mass. Such an abnormal physiologic response in a muscle group cause the muscle cells to express nicotinic acetylcholine receptors. Nicotine or nicotine acetylcholine receptor agonist is used to bind the receptors. Binding stimulates the release of growth factors, including human growth hormone (HGH), vascular endothelial growth factor (VEGF), basic fibroblast growth factors (bEGF) and other chemokines, cytokines and attractants to stem cell recruitment, migration and mobilization at the target physiologic tissue or muscle group. The stem cells differentiate into the phenotype of the mobilized target muscle group or physiologic tissues.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1

To study the effects of nicotine in the diet of mice in combination with exercise, 34 mice were divided into two equal groups. The diet of one group of mice was supplemented with nicotine added to the drinking water and the other group had plain water. Both groups received the same chow and water freely.

The experiment was a double-blind investigative study including a total of 34 healthy male mice that were approximately 9 weeks old, weighing approximately 35 grams. The mice were received one week prior to the start of the study to allow for a week of acclimation to the study site and the handlers. Because mice are active when it is dark and sleep when it is light, an automatic lighting system (12 hour dark/12 hour light) was set up for the duration of the study. The dark cycle was from 9 pm to 9 am and the light cycle from 9 am to 9 pm. The mice were subjected to a 3 week weighted exercise regimen on a treadmill wheel.

The 34 mice were divided in 2 groups of 17 mice each. Group 1 (nicotine treatment) received water laced with nicotine containing 60 micrograms nicotine/ml water and 10 mg saccharine tablet or pinch of a sugar substitute powder. The sugar substitute served to mask the bitter taste of nicotine in the water. Group 2 (placebo or control) followed the same weight exercise regimen as the nicotine treatment group. Their drinking water was plain water with the same amount of saccharine or sugar substitute as in Group 1. Each mouse had access to its water ad libitum daily during the study period, regardless of the group. Weekly water consumption was measured.

Mice in both groups were subjected to a weight/exercise regimen in the morning at the end of the dark cycle around 8:00 am. Weights were affixed to each animal at the beginning of the exercise. The weights were approximately 10% of body weight measured at Day -1 of the study, and adjusted based on body weight, measured weekly. The mice were exercised for 15 minutes per day or until exhaustion, 5 days a week for 3 weeks on a Mouse Forced Exercise Walking/Running Wheel System (Model 80800, Lafayette Instrument, North Lafayette, Ind. 47903). The largest part of the upper hind muscle of the mice was measured with a dial caliper every week. Two measurements on each leg were taken and the average was calculated.

All mice received a healthy diet (PMI Feeds, Formula #2002) ad libitum. Food consumption was measured weekly by weighing the food offered at the beginning of the week and weighing the food remaining the end of the week.

Change of Leg Diameter in Nicotine Group

Comparing with day 0, the leg diameters of day 7, 14 and 21 show significant increase as depicted in FIG. 1. Using a paired, one-sided t-test, p-value for day 7 is 0.00001, for day 14 is 0.000002. Day 21 is decreasing compared with day 14 but it is still bigger than day0, with a p-value of 0.025. With a significant level of 0.05, data from all three days show statistical significance.

Change of Leg Diameter in Control Group

Comparing with day 0, only data from day 14 show significant increase; day 21 shows significant decrease as depicted in FIG. 1. Using a paired, one-sided t-test, p-value for day 7 is 0.064, for day 14 is 0.000004. Day 21 is smaller than day 0 with a p-value of 0.015. With a significant level of 0.05, data from days 14 and 21 show statistical significance.

Comparison Between Nicotine and Control Groups

Figure 2:
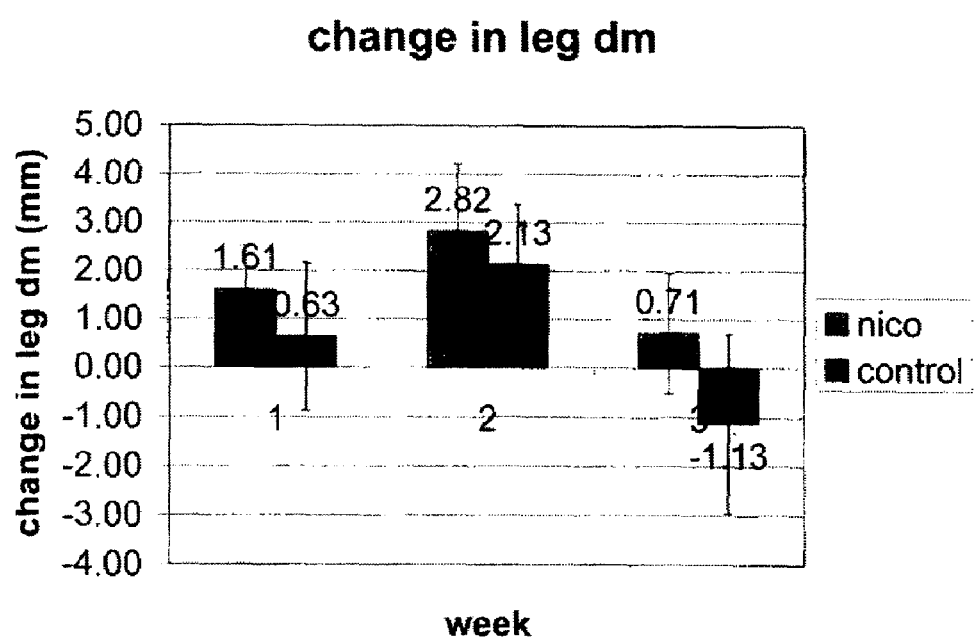
FIG. 2 is a graph illustrating the effect of a nicotine supplement on change in leg diameter of an animal model.

Referring now to FIGS. 1 and 2, on day 0, the leg diameters show no difference. Using a two-sided t-test, the p-value is 0.76. On day 7, the nicotine group shows significantly greater increase of leg diameters. Using a one-sided t-test, p-value is 0.02. Comparing to day 0, average increase is 1.6 mm for nicotine group and 0.6 mm for the control group. On day 14, the nicotine group shows a greater increase but not statistically significant. Using a one-sided t-test, p-value is 0.09 and comparing to day 0, the average increase is 2.8 mm for the nicotine group and 2.1 mm for the control group. On day 21, both groups show a decrease compared with day 14, but the control group shows a significantly greater decrease than the nicotine group. Using a one-sided, p-value is 0.002 and comparing to day 0, the nicotine group still has a 0.7 mm increase, while the control group has a 1.1 mm decrease. Taking the average leg diameters of the mice from day 7, 14 and 21, and comparing the average leg diameters with day 0, both the nicotine and the control group show a increase. Using a one-sided t-test, the nicotine group show a significantly greater increase, with a p-value of 0.001. The average increase for the nicotine group is 1.7 mm while the average increase of the control group is 0.5 mm. Overall, the nicotine group shows a significantly greater increase in leg diameter.

Food Consumption

Figure 3:
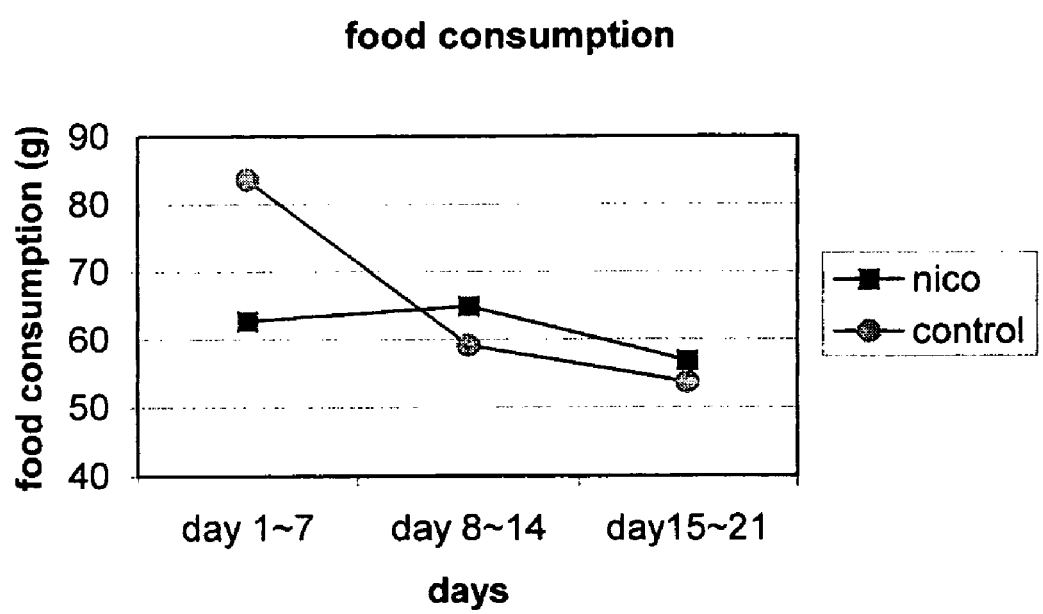
FIG. 3 is a graph illustrating the effect of a nicotine supplement on food consumption of an animal model.

Referring now to FIG. 3, food consumption in the nicotine group does not show significant change over time. In the control group, food consumption shows a general decreasing trend over time. Comparing to days 1~7, days 15~21 show significantly lower food consumption with a p value of 0.03. When taking the average food consumption, there is no significant difference between the nicotine group and the control group. However, when taking the difference of food consumption from days 15~21 to day 1~7, and using a one-sided t-test, a significant difference between the nicotine group and the control group is observed, with a p value of 0.045. On average, compared to days 1~7, the control group consumed 30 grams less of food in days 15~21; while the nicotine group consumed only 6 grams less.

Example 2

In order to determine the effects of a nicotine supplement on human subjects, a double blind placebo controlled study was conducted. The study tested 32 males aged 30–59 years old. Each participant needed to have been weight-lifting and exercising on a consistent basis for at least one full year prior to the study. The study required each of the 32 males to remain consistent with their current exercise program (minimum of 3x's per week), required not to add any new exercises to their current program, not add any new supplements to their diet during the six week study and to take the nicotine supplement 30 minutes prior to exercise. The nicotine supplement was 3 micrograms of nicotine in a standard 300 mg capsule containing polyethylene gycol (PEG) as a vehicle. The placebo capsule was identical in all aspects but contained no active (nicotine) ingredients.

The 32 males were subdivided into 4 groups, 2 placebo groups (8 took 1 capsule and 8 took 2 capsules with no active nicotine ingredients prior to exercise). In the other two groups (active), 8 subjects took 3 micrograms of nicotine and 8 took 6 micrograms of nicotine prior to exercise. The individuals were tested in the beginning and conclusion of the study in the following areas: (1) overall body fat/lean muscle ratio (ELG impedance test was used, which is 98% accurate compared to skinfold testing); (2) biceps; (3) upper leg muscle mass; and (4) 10 exercise repetition maximum, for both upper and lower body strength test (bench press and leg press). Participant workouts were logged by each individual in their own notebooks, to ensure consistency and compliance The test results are summarized in the following tables:

TABLE 1

Comparisons Among Study Groups

| Change Over Study (Post-Pre)* | Nicotine (1 Cap.) (n = 8) | Nicotine (2 Cap.) (n = 8) | Placebo (1 Cap.) (n = 8) | Placebo (2 Cap.) (n = 7) | p** |
|---|---|---|---|---|---|
| Upper-body Strength | 10.00 (5.00, 20.00) | 10.00 (5.00, 20.00) | 7.50 (0.00, 15.00) | 0.00 (0.00, 10.00) | 0.097 |
| Lower-body Strength | 65.00 (15.00, 90.00) | 80.00 (20.00, 320.00) | 50.00 (10.00, 65.00) | 10.00 (0.00, 20.00) | 0.001 |
| Bicep Circumference (cm) | 0.45 (−0.20, 2.00) | 0.63 (−1.50, 1.70) | 0.00 (−1.00, 0.50) | 0.00 (−0.70, 1.00) | 0.282 |
| Quadricep Circumference (cm) | 0.00 (−2.00, 2.50) | 0.00 (−2.00, 3.00) | 0.00 (−1.00, 0.50) | 0.00 (−2.00, 2.00) | 0.936 |
| Body Fat % | −0.65 (−1.90, 0.70) | −1.05 (−5.90, 0.10) | −0.10 (−3.20, 1.10) | −0.40 (−1.60, 1.20) | 0.599 |
| Lean Mass % | 0.65 (−0.70, 1.90) | 1.05 (−0.10, 5.90) | 0.10 (−1.10, 3.20) | 0.40 (−1.20, 1.60) | 0.640 |
| Weight (lbs) | −1.00 (−6.00, 3.00) | −0.50 (−8.00, 6.75) | 0.00 (−4.00, 4.00) | −2.00 (−8.00, 1.00) | 0.695 |
| Body Mass Index | −0.13 (−0.79, 0.45) | −0.08 (−1.22, 0.94) | 0.00 (−0.62, 0.56) | −0.29 (−1.21, 0.14) | 0.669 |

*Median (Range)
**Based on Kruskal-Wallis Oneway Analysis of Variance

TABLE 2

Post hoc Analysis - Lower-body Strength

| Paired Comparison | p* |
|---|---|
| Nicotine (1 Cap.) vs. Nicotine (2 Cap.) | 0.164 |
| Nicotine (1 Cap.) vs. Placebo (1 Cap.) | 0.053 |
| Nicotine (1 Cap.) vs. Placebo (2 Cap.) | 0.001 |
| Nicotine (2 Cap.) vs. Placebo (1 Cap.) | 0.042 |
| Nicotine (2 Cap.) vs. Placebo (2 Cap.) | <0.001 |
| Placebo (1 Cap.) vs. Placebo (2 Cap.) | <0.001 |

*Bonferroni correction: $\alpha^* = 0.05/6 = 0.008$, values are 1-tailed

TABLE 3

Comparisons Between Nicotine (1 or 2 Capsules) and Placebo (1 or 2 Capsules)

| Change Over Study (Post-Pre)* | Nicotine (n = 16) | Placebo (n = 15) | p** |
|---|---|---|---|
| Upper-body Strength | 10.00 (5.00, 20.00) | 5.00 (0.00, 15.00) | 0.025 |
| Lower-body Strength | 70.00 (15.00, 320.00) | 20.00 (0.00, 65.00) | <0.000 |
| Bicep Circumference (cm) | 0.45 (−1.50, 2.00) | 0.00 (−1.00, 1.00) | 0.030 |
| Quadricep Circumference (cm) | 0.00 (−2.00, 3.00) | 0.00 (−2.00, 2.00) | 0.286 |
| Body Fat % | −0.95 (−5.90, 0.70) | −0.40 (−3.20, 1.20) | 0.190 |
| Lean Mass % | 0.95 (−0.70, 5.90) | 0.40 (−1.20, 3.20) | 0.260 |
| Weight (lbs) | −0.75 (−8.00, 6.75) | 0.00 (−8.00, 4.00) | 0.446 |
| Body Mass Index | −0.11 (−1.22, 0.94) | 0.00 (−1.21, 0.56) | 0.415 |

*Median (Range)
**Based on Wilcoxon Rank Sum Test (Mann-Whitney U), using 1-tailed values.

Significant differences from baseline to post-test were observed in the 4-group analysis For Lower-body Strength, with post hoc analysis demonstrating differences between Nicotine (1 Cap.)-Placebo (2 Cap.), Nicotine (2 Cap.)-Placebo (1 Cap.), Nicotine (2 Cap.)-Placebo (2 Cap.), and Placebo (1 Cap.)-Placebo (2 Cap.). A second analysis was performed, comparing baseline to post-test differences between subjects receiving Nicotine (1 or 2 Cap.) and those receiving Placebo (1 or 2 Cap.). Significant differences were observed for Upper-body Strength, Lower-body Strength, and Bicep Circumference.

The study had a high compliance and completion rate. The subjects remained consistent with their exercise program, took the nicotine supplement daily and 31 of the 32 individuals completed the study. The test results were highly conclusive in demonstrating the efficacy of the nicotine supplement. Fifteen of the sixteen individuals in the active (nicotine) group made significant changes in either body, strength levels or muscle mass or in all three test areas. In contrast, only five of the sixteen individuals in the placebo group made a significant change in either bodyfat, strength levels or muscle mass, or in all three test areas. The two groups that took 2 capsules (both placebo and active), were the most athletic and leanest of the study participants. It was in comparing these two groups the most pivotal outcome in the study was discovered. The results demonstrate that the active (nicotine) group which took 2 capsules (6 micrograms of nicotine), demonstrated the most significant gains of any group.

In summary, five subjects increased leg strength over 25%, two of them by 40%. One subject changed his overall body fat by 32% and seven of the eight made impressive changes in body measurements during the six-week study. Also, 13 of the 16 subjects in the active (nicotine) group noted an increases in their overall endurance, leg strength and noted a strong thermogenic effect (increased basal metabolic rated) during the study. The thermogenic effect may be enhanced by combining the injestion of up to one milligram of nicotine with 100 milligrams of caffeine.

While a preferred embodiment of the invention has been shown and described, other and further embodiments of the invention may be devised without departing from the basic scope thereof. It s to be understood that this invention is not limited to particular methodologies (e.g., modes of administration) or specific compositions described, as such may, of course, vary. It is also to be understood that the terminology used herein is for the purpose of describing particular embodiments only, and is not intended to be limiting, since the scope of the present invention will be limited only by the appended claims.

The invention claimed is:

1. A method of developing muscle mass in a mammal by stimulating, recruiting and mobilizing muscle cells to a specific muscle mass, the method comprising administering nicotine or nicotine acetylcholine receptor agonist (nAChR) to a mammal in an amount sufficient combined with exercise to increase said specific muscle mass.

2. The method of claim 1 wherein the muscle cells are differentiated from endogenous stem cells.

3. The method of claim 1 wherein said muscle cells are recruited to said specific muscle mass in response to said exercise of said specific muscle mass.

4. The method of claim 3 wherein said exercise stimulates the muscle cells of said specific muscle mass to express nicotinic acetylcholine receptors.

5. The method of claim 4 including the step of administering nicotine or a nAChR agonist to bind said nicotinic acetylcholine receptors.

6. The method of claim 5 wherein said binding stimulates the release of growth factors, including human growth hormone (HGH), vascular endothelial growth factor (VEGF), basic fibroblast growth factors (bFGF) and other chemokines, cytokines and attractants to stem cell recruitment, migration and mobilization at said specific muscle mass.

7. The method of claim 2 wherein said stem cells differentiate into the phenotype of said specific muscle mass.

8. The method of claim 3 wherein said exercise stimulates said specific muscle mass to release metabolites, catecholamines, cytokines, chemokines, and/or cause an inflammatory response in said specific muscle mass.

9. The method of claim 1 wherein the nicotine or nicotine acetylcholine receptor agonist (nAChR) is administered in an amount sufficient to produce increased thermogenesis.

* * * * *